(12) United States Patent
Link et al.

(10) Patent No.: US 8,652,835 B2
(45) Date of Patent: Feb. 18, 2014

(54) DEVICE AND METHOD FOR THE MECHANICAL DECOLLATION OF CELLS FROM A CELL COMPOSITE

(75) Inventors: Holger Link, Hamburg (DE); Alexander Papra, Hamburg (DE); Michael Blumentritt, Hamburg (DE); Vinh Duong, Hamburg (DE)

(73) Assignee: Eppendorf AG (DE)

( * ) Notice: Subject to any disclaimer, the term of this patent is extended or adjusted under 35 U.S.C. 154(b) by 1101 days.

(21) Appl. No.: 12/525,595

(22) PCT Filed: Jan. 31, 2008

(86) PCT No.: PCT/EP2008/000791
§ 371 (c)(1),
(2), (4) Date: Aug. 3, 2009

(87) PCT Pub. No.: WO2008/092697
PCT Pub. Date: Aug. 7, 2008

(65) Prior Publication Data
US 2010/0087003 A1    Apr. 8, 2010

(30) Foreign Application Priority Data
Feb. 2, 2007    (DE) .......................... 10 2007 005 369

(51) Int. Cl.
| | |
|---|---|
| B01D 15/08 | (2006.01) |
| B01D 63/00 | (2006.01) |
| C02F 1/44 | (2006.01) |
| C12M 1/00 | (2006.01) |
| C12M 3/00 | (2006.01) |
| C12M 1/36 | (2006.01) |
| C12M 1/38 | (2006.01) |
| C12N 5/00 | (2006.01) |
| C12N 5/02 | (2006.01) |

(52) U.S. Cl.
USPC ................ 435/308.1; 210/198.2; 210/321.63; 210/321.75; 435/283.1; 435/286.1; 435/286.7; 435/379

(58) Field of Classification Search
USPC .......... 435/283.1, 286.1, 286.7, 289.1, 308.1, 435/379; 210/198.2, 321.63, 321.75
See application file for complete search history.

(56) References Cited

U.S. PATENT DOCUMENTS

| | | | |
|---|---|---|---|
| 4,028,190 A | 6/1977 | McAleer et al. | |
| 4,072,275 A | 2/1978 | Bartels et al. | |

(Continued)

FOREIGN PATENT DOCUMENTS

| | | |
|---|---|---|
| DE | 3218079 A1 | 12/1982 |
| DE | 202006013102 | 12/2006 |

(Continued)

Primary Examiner — Nathan Bowers
Assistant Examiner — Lydia Edwards
(74) Attorney, Agent, or Firm — Hiscock & Barclay, LLP

(57) ABSTRACT

A device for mechanically decollating cells from a cell composite, particularly a shear rotor, a cell isolation unit including such a shear rotor and a method for decollating cells from a cell composite. The aforementioned device includes a rotor having a rotor wall, which is concentrically arranged in a receptacle. A rotor seat is connected to a motor and to which the rotor can be fixed in a detachable manner. A rotational movement of the motor can be transmitted to the rotor by means of the rotor seat. The rotor tapers longitudinally towards the bottom of the receptacle so that different circumferential speeds of the rotor can be transmitted to a liquid sample in the receptacle via the rotor wall.

8 Claims, 3 Drawing Sheets

(56) References Cited

U.S. PATENT DOCUMENTS

Figure 1:
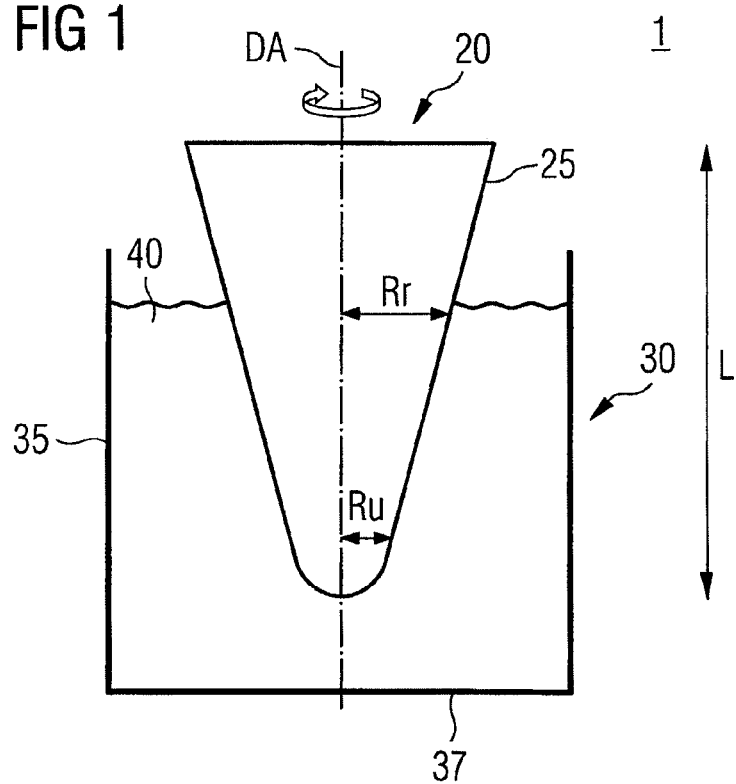

| | | | |
|---|---|---|---|
| 4,541,541 A * | 9/1985 | Hickman et al. | 220/253 |
| 4,678,559 A | 7/1987 | Szabados | |
| 4,696,666 A * | 9/1987 | Rice, Jr. | 494/16 |
| 5,030,361 A * | 7/1991 | Ishida et al. | 210/772 |
| 5,879,939 A | 3/1999 | Gray et al. | |
| 5,888,409 A | 3/1999 | Morsiani et al. | |
| 6,193,883 B1 * | 2/2001 | Kroner et al. | 210/198.2 |
| 6,358,474 B1 | 3/2002 | Dobler et al. | |
| 6,535,796 B1 * | 3/2003 | Sierro et al. | 700/281 |
| 2003/0166269 A1 | 9/2003 | Deckwer et al. | |
| 2005/0032200 A1 | 2/2005 | Sun et al. | |
| 2006/0245980 A1 * | 11/2006 | Kiselev et al. | 422/130 |

FOREIGN PATENT DOCUMENTS

| | | |
|---|---|---|
| EP | 0191941 A1 | 8/1986 |
| WO | WO 00/68358 A1 | 11/2000 |

\* cited by examiner

DEVICE AND METHOD FOR THE MECHANICAL DECOLLATION OF CELLS FROM A CELL COMPOSITE

CROSS REFERENCE TO RELATED APPLICATIONS

This application is based upon and claims priority under 35 USC §119 to PCT/EP2008/000791, filed Jan. 31, 2008 entitled: DEVICE AND METHOD FOR THE MECHANICAL DECOLLATION OF CELLS FROM A CELL COMPOSITE, which is based upon German Patent Application No. 10 2007 005 369.1, filed Feb. 2, 2007 entitled: DEVICE AND METHOD FOR THE MECHANICAL DECOLLATION OF CELLS FROM A CELL COMPOSITE. The entire contents of each above noted application is herein incorporated by reference.

FIELD OF THE INVENTION

The present invention relates to devices and a method for decollating cells from a cell composite using a shear rotor.

BACKGROUND OF THE INVENTION

For various experimentation purposes it is necessary to decollate cells present in a cell composite. The state of the art offers different methods for this purpose. Among these methods are for example, the ultrasonic treatment of a cell composite according to the U.S. Pat. No. 5,879,939, multiple filtration through filters of different pore sizes according to the U.S. Pat. No. 5,888,409, the diminution or shredding of a cell composite according to the U.S. Pat. No. 4,028,190, or the shearing of a liquid sample with the cell composite by means of pipetting or a shear rotor according to the German patent DE 32 18 079.

The above named methods have different disadvantages. On the one hand, the cell composite present in the liquid sample is frequently overstressed by the energy applied for decollating. This leads to a destruction of the cells, and to a lengthening of the preparation method until intact decollated cells are available. The above disadvantage occurs precisely during mechanical decollating methods, as in the above named diminution device, or during pipetting of the liquid sample.

The shear rotor according to DE 32 18 079 has the disadvantage that a liquid sample with the cell composite is subjected everywhere to the same shear forces. In addition, the sample is moved due to turbulent flows within the shear rotor such that a uniform sample processing is not guaranteed.

Therefore, it is the objective of the present invention to provide a device and a method for decollating cells from a cell composite, with which, in comparison to the state of the art, samples can be processed more reliably.

SUMMARY OF THE INVENTION

The above objective is solved by devices and methods according to the claims. Advantageous embodiments and further developments of the present invention are described in the following description, the drawings and the dependent claims.

According to one aspect, the present invention discloses a device for mechanical decollating of cells from a cell composite, in particular a shear rotor, which has the following features: a rotor with a rotor wall, where the rotor is disposed concentrically in a receptacle, a motor connected to a rotor seat, to which the rotor can be fastened in a detachable manner and by which a rotational movement of the motor can be transmitted to the rotor, while the rotor tapers in the longitudinal direction towards the bottom of the receptacle, so that different circumferential speeds of the rotor can be transmitted via the rotor wall to a liquid sample in the receptacle. Decollating of cells can be understood as isolating or separating cells from a cell composite, particularly a tissue.

The shear rotor described above includes a receptacle in which a liquid sample with a cell composite is received. Within the receptacle, a rotor is disposed rotatably, so that through the rotation of the rotor within the receptacle the cell composite in the liquid sample is sheared, and is decollated into individual cells. Furthermore, the geometry of the rotor guarantees that a circulation of the liquid sample within the receptacle occurs, and thus, also within the gap between the rotor wall and the wall of the receptacle. In this way, the entire volume of the sample is processed and the formation of residues, for example at the bottom of the receptacle, is prevented. For this purpose, the rotor has a structure which tapers downwards, preferably cone-shaped. With a rotation of the rotor, due to its geometry, two imaginary points on the rotor wall move at different speeds if they are disposed with different distances from the bottom of the receptacle. Based on the different rotational speeds which increase with increasing distance from the bottom, pressure differences result in the receptacle and in the gap between the rotor wall and the receptacle wall, which lead to an advantageous circulation and shearing of the liquid sample.

According to different embodiments, the receptacle has a cylindrical form or a form of lower conicity compared to the cone-shaped rotor, or widens in the direction of the bottom of the receptacle.

According to another embodiment, the rotor and/or receptacle can be produced from a single-use material, for example from plastic or PVC, in order to be able to dispose of this after processing a liquid sample. The use of a rotor and/or receptacle from a single-use material requires that the rotor can be fastened and detached from the rotor seat with minimal effort, for example, automatically. For this purpose, the rotor seat has an outside thread, and the rotor has an inside thread matched to the outside thread. According to another alternative, the rotor seat includes a projection, and the rotor has a snap fit matched to the projection, such that the rotor can also be fastened detachably to the rotor seat. In the case of the simple connection of the rotor seat and the rotor using a snap fit, the rotor seat additionally includes a rotational interlock, with which the rotational movement of the rotor seat can be transmitted to the rotor on the basis of a positive locking and/or non-positive locking connection.

In addition, it is preferable, to provide the above mentioned device with auxiliary technical means for performing a turbidity measurement of the liquid sample in the receptacle. For this purpose, the receptacle is produced from a material that can be at least partially penetrated by radiation. According to an alternative, this material can be penetrated by radiation in the visual range, or has a plurality of windows, so that using a light source and an appropriate sensor for recording the quantity of light, a turbidity measurement can be performed on the liquid sample. Furthermore, it is conceivable to perform the turbidity measurement using ultrasound, so that the receptacle must be produced from an ultrasound-permeable material. The turbidity measurement is performed and monitored, for example, by a control unit or a computer, and the data that is collected is appropriately evaluated.

The present invention further discloses a cell isolating unit for mechanical decollating of cells from a cell composite, where the unit has the following characteristics: a rotor with a rotor wall where the rotor can be disposed automatically and in a movable manner into a plurality of receptacles with a receptacle wall, a motor connected to a rotor seat, to which the rotor can be fastened in a detachable manner and by which a rotational movement of the motor can be transmitted to the rotor, while the plurality of receptacles is disposed in a receptacle holder, so that via an automatic movement of the rotor and/or the receptacle holder, the rotor can be positioned and rotated concentrically in each one of the receptacles, respectively, of the receptacle holder.

The cell isolation unit described above provides the possibility to systematically, successively process a plurality of liquid samples with cell composites with the shear rotor according to the invention. The different liquid samples are disposed in different receptacles within a receptacle holder. Advantageously, the receptacles are arranged regularly such that each individual receptacle position can be selectively reached, for example, using a control module or a computer control. The processing of the liquid sample with the cell composite can occur in the selected receptacle as soon as the rotor is disposed concentrically within the selected receptacle, either due to its own movement, a movement of the receptacle holder, or a combined movement of the rotor seat and receptacle holder.

According to a first alternative, the rotor of the cell isolation unit has a cylindrical form. Furthermore, it is preferred that the rotor tapers in its longitudinal direction towards the bottom of the receptacle, and in particular, is preferably designed cone-shaped. These different rotor forms can be combined with receptacles which, in each case, have an opening only on their upper side for filling the receptacle with a liquid sample. According to different embodiments, the receptacles have a cylindrical form, or a form that tapers towards the bottom of the receptacle, in particular, a cone-shaped form. It is also conceivable to design the receptacle such that it expands in the direction of its bottom.

According to a further embodiment, the receptacle holder is designed as a circular holder in which the plurality of receptacles is arranged removably in matched openings, equally spaced along a circular shaped track. It is also conceivable to design the receptacle holder as an angular holder so that the plurality of receptacles is disposed along straight lines, for example, equidistant from each other. The specified geometry of the receptacle holder dictates the exact position of the individual receptacles, so that the rotor can be positioned automatically in the individual receptacles with minimal effort, for example, computer controlled. Furthermore, such a design opens up the possibility to fill different receptacles with different samples and/or to process different receptacles with specially adapted decollating methods.

According to a further embodiment, the cell isolation unit includes an exchange device, with which the rotor and/or the receptacle can be removed and replaced by a new rotor and/or a new receptacle, respectively. Such an exchange device forms the prerequisite for further automation of the processing of a plurality of liquid samples, if these are supplied, for example, by an automatic dosing device into the newly installed receptacles.

Furthermore, it is preferred to equip the cell isolation unit with a temperature control unit so that a liquid sample in one or a plurality of receptacles in the receptacle holder can be temperature controlled in a targeted manner.

The present invention also discloses a method for decollating cells from a cell composite that has the following steps: introduction of a liquid sample with a cell composite into a receptacle, the concentric arrangement of the rotor, which tapers in its longitudinal direction towards the bottom, in the receptacle so that different circumferential speeds of the rotor are transmitted via a rotor seat to a liquid sample in the receptacle, and rotation of the rotor, such that the cell composite is decollated into cells. According to a preferred alternative of the method for decollating described above, a rotational speed of the rotor in the receptacle and the geometry of the rotor are matched to each other such that the liquid sample is circulated and sheared within the gap during the rotation of the rotor. This guarantees a processing of the entire sample and prevents unprocessed residues of the liquid sample, for example, on the bottom of the receptacle.

DESCRIPTION OF THE ACCOMPANYING DRAWINGS

The present invention is explained in more detail in reference to the accompanying drawings.

Figure 2A:
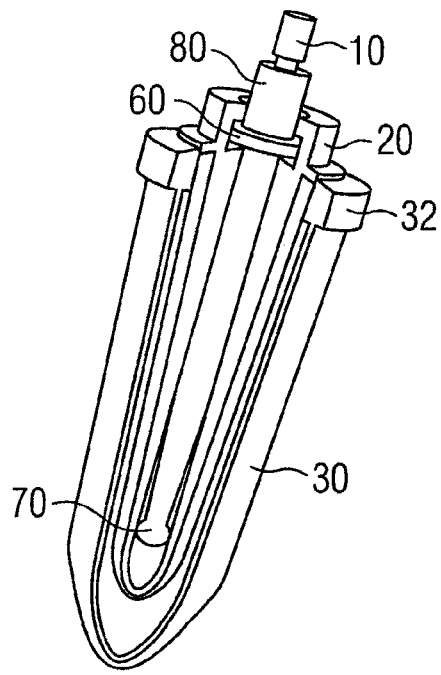
Figure 2B:
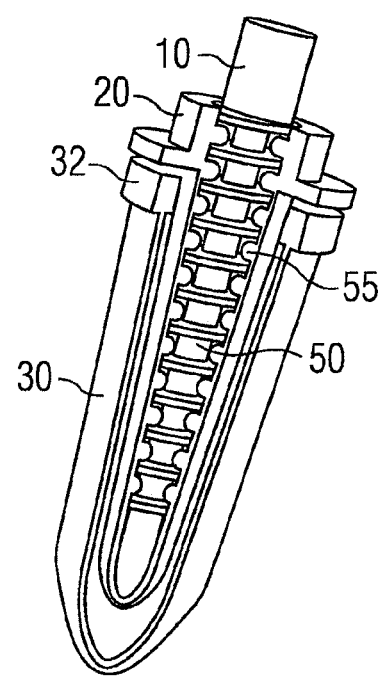
Figure 3:
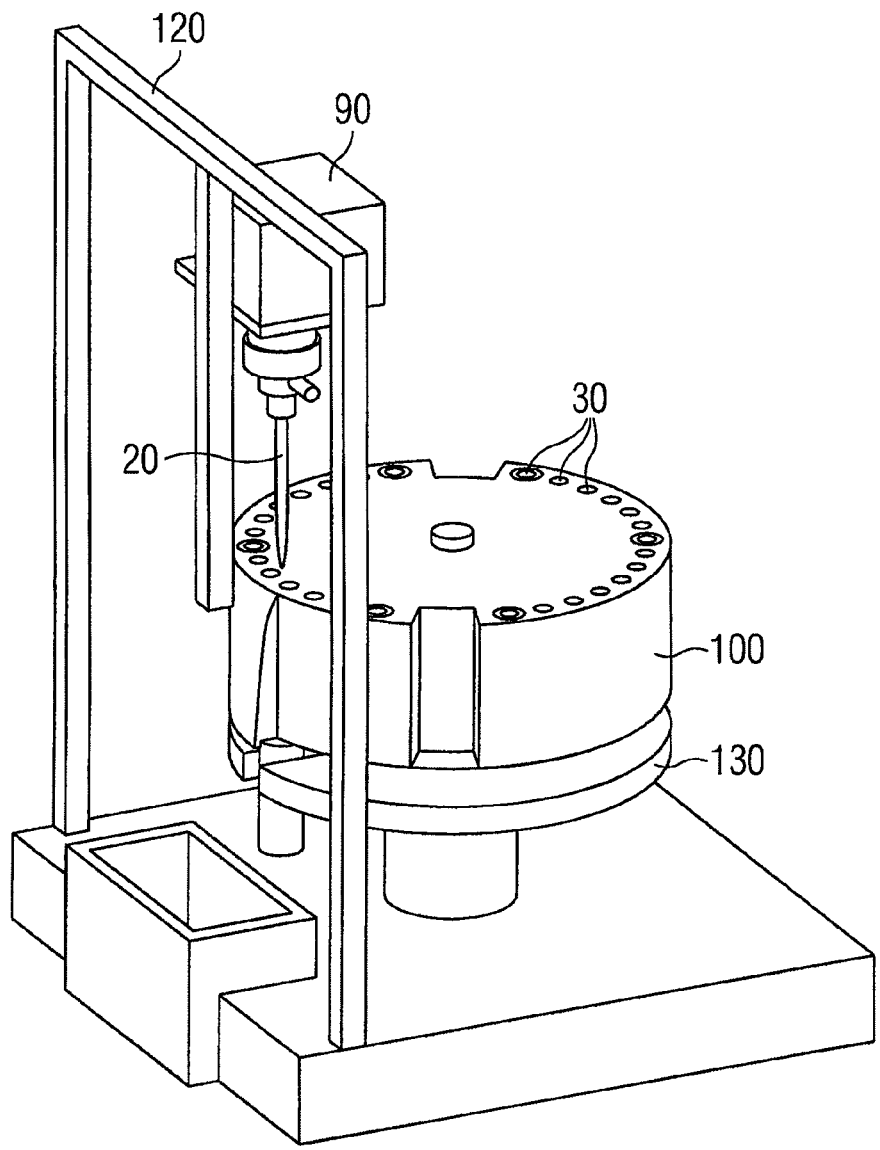
Figure 4:
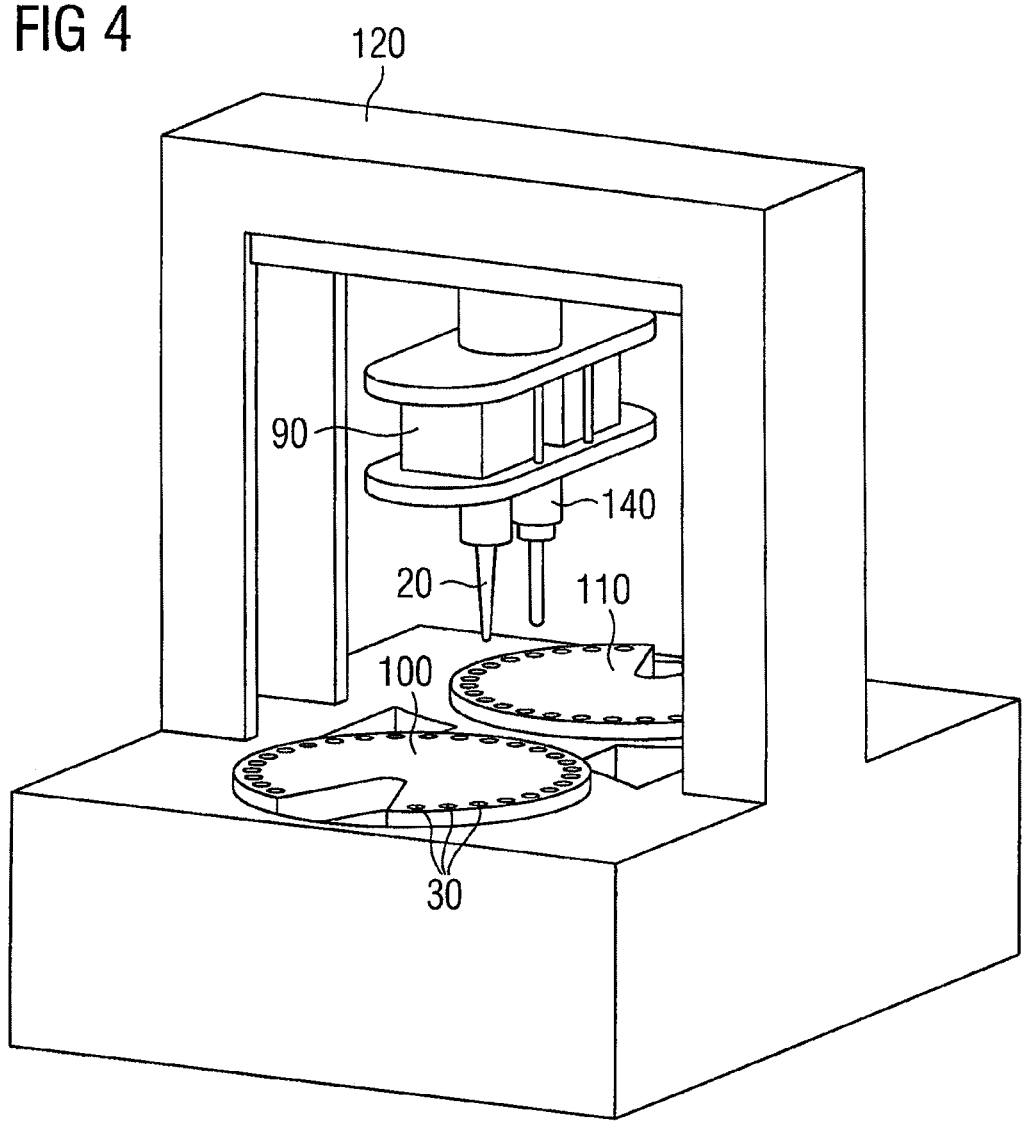

FIG. 1 is a schematic sectional representation of the shear rotor according to the invention, FIG. 2 A, B each depict a perspective representation of an embodiment of the shear rotor according to the invention, FIG. 3 illustrates an embodiment of the cell isolation unit, and FIG. 4 illustrates another embodiment of the cell isolation unit.

DETAILED DESCRIPTION OF PREFERRED EMBODIMENTS

FIG. 1 shows a schematic representation of an embodiment of the shear rotor 1 according to the invention. The shear rotor 1 comprises a receptacle 30 and a rotor 20, which is disposed concentrically and rotatably within the receptacle 30. The receptacle 30 preferably has a cylindrical interior contour, while the bottom 37 of the receptacle 30 is designed to have a conical or hemispherical shape. It is also preferred that the receptacle 30 is designed to have a conical shape or a shape that widens in the direction of the bottom 37. The rotor 20 is fixed to a rotor seat 10 (not shown, see below) in a detachable manner. The rotor seat 10, in turn, is connected to a motor 90 (not shown), so that a rotational movement of the motor 90 can be transmitted to the rotor 20.

The rotor 20 is circumferentially delimited by a rotor wall 25. The rotor wall 25 is distanced from a rotational axis DA, represented by a dash-dot line, of the rotor 20 by the radius R. The rotor 20 tapers extending in the direction of its longitudinal axis L and towards the bottom 37 of the receptacle 30. According to a preferred alternative, the rotor 20 is designed cone-shaped. Due to the tapered shape of the rotor 20, the rotor wall 25 at a larger distance from the bottom 37 is offset from the rotational axis DA by the radius $R_o$, which is greater than a radius $R_u$ at a smaller distance from the bottom 37.

If the rotor 20 is now rotated by the motor about the rotational axis DA, a point on the rotor wall 25 with the offset $R_o$ from the rotational axis DA moves faster than a point on the rotor wall 25 with the offset $R_u$ from the rotational axis DA. Due to the faster circumferential speed in the upper region of the rotor 20 in comparison to its tapered region, there arises a dynamic pressure distribution in the liquid sample 40 in the receptacle 30. Due to this pressure distribution, the portions of the liquid 40 near the bottom 37 of the receptacle 30 are moved or suctioned into the gap between the rotor wall 25 and the receptacle wall 35 in the direction of surface of the liquid. Within the gap between the rotor wall 25 and the receptacle wall 35, the liquid sample 40 with the cell composite is subjected to shear forces which lead to a decollating of the cells. Portions of the liquid sample 40 near the receptacle wall 35 sink again towards the bottom 37, resulting in a circulation of the liquid sample 40. If the rotational speed and the geometry of the rotor 20 are matched to each other, the circulation and shearing of the liquid sample 40 in the receptacle 30 can be adjusted in a directed way. This guarantees that the liquid sample 40 is moved also in a receptacle 30 with only an upper opening in the gap between the receptacle wall 35 and the rotor wall 25, without the receptacle 30 having an inlet or a pressure supply near the bottom 37. In addition, sufficient shear forces are generated in the liquid sample 40 using the planar rotor wall 25 and receptacle wall 35, in order to decollate the cells. Additionally, it is also conceivable to design the rotor wall 25 with projections and/or profiles, in order to process the liquid sample 40.

The rotor 20 and the receptacle 30 are preferably produced from plastic, in particular PVC. In addition, the rotor 20 and the receptacle 30 can be produced as single-use or multi-use articles, which can be manually or automatically exchanged.

According to one embodiment the receptacle 30 is composed of a material that can be permeated by ultrasonic waves or light, in order to be able to perform a turbidity measurement of the liquid sample 40 in the receptacle 30. Ultrasound or light is directed through the radiation permeable material at the liquid sample 40. The reflected ultrasonic waves are recorded, for instance, by the ultrasound head that was previously used as the ultrasound source, and are converted into an electrical signal. This electrical signal is supplied for analysis purposes to, for example, a computer or a computing unit. If the turbidity measurement is performed optically, light is radiated through the receptacle wall 35 into the liquid sample 40, and the occurrence of scattered light, or a portion of the light that penetrated, or the light absorption occurring in the liquid sample 40, is subsequently recorded using a sensor. Depending on the light signal recorded in the sensor, an electrical signal is generated that in turn, is further supplied to an evaluation unit. The evaluation unit then generates a corresponding signal which represents the result of the turbidity measurement. The result of the turbidity measurement yields information about the decollation of cells and/or the mixing of the liquid sample 40 in the receptacle 30.

It is also conceivable to provide at least one window in the receptacle 30 instead of a radiation permeable material of the receptacle 30. The turbidity measurement described above can be performed using the at least one window, or with two windows lying across from each other.

According to a further embodiment, the receptacle 30 is connected to a temperature-control unit. This unit generates the desired temperature in the liquid sample 40, so that the desired test conditions can be attained.

FIG. 2 shows a preferred embodiment of the rotor 20, the rotor seat 10, and the receptacle 30. The receptacle 30 has a cone-shaped form with an upper rim 32. The rim 32 serves for supporting and stabilizing the receptacle 30 in a holder, for example in an opening of a circular holder, which is described below in more detail. Based on this geometry of the receptacle 30, it can be positioned manually or automatically into a receptacle holder, or a circular holder (see below), and can be removed again.

According to the first alternative of the rotor seat 10 represented in FIG. 2A, it includes a circumferential projection 60, which serves as a snap lock for the rotor 20. The rotor 20 has an elastic edge region or snap fit 80, formed in complement to the projection 60, which acts together in a positive lock or non-positive lock with the projection 60. So that the rotational movement of the motor connected to the rotor seat 10 can be transmitted to the rotor 20, the rotor seat 10 includes a rotational interlock 70. This rotational interlock 70 has the shape of a nub, as indicated in FIG. 2A. The rotational interlock 70 clamps in a positive locking or non-positive locking manner in the interior of the rotor 20, for example in a bulge or recess provided for this. In this way, the rotor seat 10, using the rotational interlock 70, entrains the rotor 20, so that the rotor carries out the rotational movement of the motor.

According to a further embodiment represented in FIG. 2B, the rotor seat 10 includes an outside thread 50. The rotor 20 includes an inside thread 55 matched to the outside thread 50. Therefore the rotor 20 can be attached with minimal effort to the rotor seat 10 by a threaded connection.

Based on the embodiment described above of the rotor seat 10 and the rotor 20, the rotor 20 can be fastened manually or automatically to the rotor seat 10, and can be removed from it.

The present invention further discloses a cell isolation unit for the mechanical decollation of cells from a cell composite. The cell isolation unit represents a component for the automated dissociation of liquid samples 40 with cell composites. Further components, not represented here, are conceivable, that could be combined with the cell isolation unit in order to provide an automated sample processing. These components serve, for example, for the automated receiving, supplying, and dosing of reagents and liquid samples, the temperature control, and mixing of samples, and separating the sample components, for example by centrifuging.

According to a first embodiment represented in FIG. 3, the cell isolation unit includes the rotor 20, already described above, which is connected to a motor 90 via the rotor seat. The motor 90 with the rotor seat and the rotor 20 can be moved automatically along a guideway 120 at least in the vertical direction. It is further conceivable, that the motor 90 is provided to be movable also in the horizontal direction. Using the vertical movement of the rotor 20 along the guideway 120, the rotor 20 can be lowered into individual receptacles 30, in order to be disposed there, as described above, and to perform a decollation of cells in a liquid sample.

A plurality of receptacles 30 of the cell isolation unit is disposed regularly or irregularly in a receptacle holder 100. The receptacle holder 100 is preferably designed as a circular holder, in which the receptacles 30 are disposed in openings that are equidistant from each other along a circular track. The openings are matched to the receptacles 30, so that the receptacles 30 can be placed into the openings, and removed from them, with minimal effort. According to different alternatives, the receptacles 30 have a cylindrical shape, a cone shape, or a shape that widens towards the bottom 37 of the receptacle 30. According to a first embodiment, the rotor has a cylindrical shape with the attachment possibilities as described above in reference to the rotor 20. According to a further embodiment, the rotor 20 described above is used.

It is additionally preferred to arrange the circular holder 100 on a platform 130 that can be moved by a motor. Using the platform 130, the circular holder 100 can be moved in a step-wise manner so that individual receptacles 30 can be positioned in a directed manner in reference to the rotor 20. According to a further alternative, the platform 130 serves as a centrifuge unit, which rotates the circular holder for separating the components of the liquid sample 40. According to a further embodiment, the platform 130 can be moved also in the vertical direction. This opens up the possibility that the rotor 20 and the motor 90 are disposed in a fixed manner, while the rotor 20 is positioned into the respectively desired receptacle 30 using the vertical and the rotational movement of the circular holder 100. This positioning can also occur using a combined movement of the rotor 20/motor 90 and the circular holder 100/platform 130.

According to a further embodiment, the cell isolation unit includes an exchange device with which the rotor 20 being used, and the receptacles 30, can be exchanged automatically. This exchange device automatically removes the rotor 20 from the rotor seat 10 and deposits it in a collection container for used single-use articles, or for multi-use articles to be cleaned. Then a new rotor 20 is automatically attached to the rotor seat 10. In the same manner, a used receptacle 30 is automatically removed and replaced by a new one.

According to a further alternative, a temperature control unit (not shown) is used together with the receptacle holder 100. This temperature control unit brings the liquid sample 40 in at least one of the receptacles 30 of the receptacle holder 100 to the desired temperature, in order to attain the desired processing conditions of the liquid sample 40.

A further embodiment of the cell isolation unit is represented in FIG. 4. In contrast to the embodiment of FIG. 3, the receptacle holder 100 and a centrifuge unit 110 are disposed next to each other. The motor 90 with the rotor 20 is disposed in an automatically movable manner along a guideway 120. A sample transfer unit 140 is provided parallel to the motor 90. Preferably, the sample transfer unit 140 can be rotated about the vertically extending attachment to the guideway 120, so that the rotor 20 or the sample transfer unit 140 can be positioned automatically over a selected receptacle 30 in the circular holder 100 or in the centrifuge unit 110. The liquid samples in the receptacles 30 in the circular holder 100 are moved step by step underneath the rotor 20. The rotor 20, in turn, is disposed into the receptacle 30 using a vertical movement, and rotated using the motor 90. In this way, the decollation of a cell composite already contained in a liquid sample can be attained. If a turbidity measurement (see above) is performed at this point on the processed liquid sample in the receptacle 30, information is obtained whether the mixture is sufficiently mixed and/or whether decollation has occurred in the liquid sample. Depending on the result of the evaluation of the turbidity measurement, the processing of the sample is either continued or ended. After successful decollation, the rotor 20 is retracted from the receptacle 30 by the vertical movement, and is exchanged for a new rotor 20 by the exchange device described above (not shown). The sample transfer unit 140 removes the liquid sample with decollated cells from the receptacle 30, and transfer it into a receptacle of the centrifuge unit 110. There, the liquid present in the sample can then be centrifuged, for instance, in order to separate the different components of the liquid sample from each other.

REFERENCE LIST

1 Device
10 Rotor seat
20 Rotor
25 Rotor wall
30 Receptacle
32 Projection
35 Receptacle wall
37 Bottom
40 Liquid sample
50 Inside thread of the rotor
55 Outside thread of the rotor seat
60 Projection
70 Rotational interlock
80 Snap fit
90 Motor
100 Receptacle holder
110 Centrifuge unit
120 Guideway
130 Platform
140 Sample transfer unit
L Longitudinal direction
DA Rotational axis of the rotor
$R_o$ Radius
$R_u$ Radius

The invention claimed is:

1. A cell isolation unit for the mechanical decollation of cells from a cell composite, said unit comprising:
a rotor body defined by a cylindrical conical form and having an inwardly tapering rotor wall, said rotor wall continually tapering from a first end to a second end and where said rotor body can be disposed automatically and movably in a plurality of receptacles, each of said receptacles having a receptacle wall; and
a rotor seat connected to a motor at one end and substantially within the rotor body at an opposing end in a detachable manner, and enabling a rotational movement of the motor to be transmitted to the rotor, the plurality of receptacles being disposed in a receptacle holder so that via an automatic movement of at least one of the rotor and the receptacle holder, said rotor can be positioned concentrically in each of the receptacles of the receptacle holder, said rotor seat being defined by a conical form complementary to said rotor, said rotor seat further including an external thread and wherein said rotor body further includes an internal thread that is matched to the external thread of said rotor seat.

2. The cell isolation unit according to claim 1, wherein the receptacle holder is circular and includes a plurality of matched openings along a circular track and in which the plurality of receptacles is removably disposed.

3. The cell isolation unit according to claim 2, wherein the circular receptacle holder is movable in a step-wise manner enabling individual receptacles to be positioned in a directed manner in reference to the rotor.

4. The cell isolation unit according to claim 1, wherein at least one of the rotor and receptacle can be automatically removed using an exchange device, and can be replaced, respectively, by a new rotor and/or a new receptacle.

5. The cell isolation unit according to claim 1, further comprising a temperature control unit with which the liquid in at least one of the receptacles can be temperature controlled.

6. A cell isolation unit for the mechanical decollation of cells from a cell composite, said unit comprising:
a rotor body defined by a cylindrical conical form and having an inwardly tapering rotor wall, said rotor wall continually tapering from a first end to a second end and where said rotor body can be disposed automatically and movably in a plurality of receptacles, each of said receptacles having a receptacle wall; and
a rotor seat connected to a motor at one end and disposed substantially within the rotor body, said rotor seat having a conical form complementary to the rotor body and disposed in a detachable manner, and enabling a rotational movement of the motor to be transmitted to the rotor the plurality of receptacles being disposed in a receptacle holder so that via an automatic movement of at least one of the rotor and receptacle holder, the rotor can be positioned concentrically in each of the receptacles of the receptacle holder and wherein said rotor seat has a projection and said rotor has an elastic edge region, allowing said rotor body to be fastened to said rotor seat in a detachable manner.

7. A method for decollating cells from a cell composite, said method comprising the steps of:

introducing a liquid sample with a cell composite from above into a receptacle, said receptacle having an upper opening for receiving said liquid sample;

concentrically disposing a rotor defined by an elongate cylindrical rotor body having a conical rotor wall that tapers continually and longitudinally from a first end at a second end, into the receptacle so that different circumferential speeds of the rotor can be transmitted via a rotor wall to a liquid sample in the receptacle, said rotor being connected through a rotor seat substantially disposed within said rotor body to a motor that enables rotation of said rotor and wherein said rotor seat has a conical form that is complementary to the rotor; and rotating the rotor so that the cell composite is decollated into cells.

8. The method for decollation according to claim 7, including the further step of matching a rotational speed of the longitudinally tapering rotor body in the receptacle and the geometry of said rotor to each other based on the conical shape of the rotor body so that the liquid sample circulates within the receptacle during the rotating step.

* * * * *